United States Patent [19]

Kuhn

[11] 3,960,151

[45] June 1, 1976

[54] METHOD AND MEANS FOR THE REPAIR OF PERIPHERAL NERVES

[75] Inventor: William E. Kuhn, Lexington, Ky.

[73] Assignee: Hemotec, Inc., Englewood, Colo.

[22] Filed: Mar. 7, 1975

[21] Appl. No.: 556,485

Related U.S. Application Data

[63] Continuation-in-part of Ser. No. 414,246, Nov. 9, 1973, Pat. No. 3,916,905.

[52] U.S. Cl. .............................. 128/334 R; 29/282; 128/297; 128/303 R
[51] Int. Cl.² ......................................... A61B 17/12
[58] Field of Search......... 128/276, 297, 299, 303 R, 128/334 R, 321, 322; 29/235, 282

[56] References Cited
UNITED STATES PATENTS

| | | | |
|---|---|---|---|
| 1,294,284 | 2/1919 | Logeman | 128/297 |
| 3,361,133 | 1/1968 | Kimberley et al. | 128/346 |
| 3,786,817 | 1/1974 | Palma | 128/334 R |
| 3,805,793 | 4/1974 | Wright | 128/334 R |

Primary Examiner—Dalton L. Truluck
Attorney, Agent, or Firm—Melville, Strasser, Foster & Hoffman

[57] ABSTRACT

A method and means for the repair of severed peripheral nerves utilizing a porous, thin walled, bridge conduit or tube and an applicator instrument therefor. The instrument is connected to a vacuum source and has means for supporting the tube in the region of the transverse hole therein. When supported by the instrument the interior of the tube is operatively connected to the vacuum source through the transverse hole and a pressure differential is created between the interior of the tube and the ambient atmosphere by means of the vacuum source. This pressure differential is used to draw one end of the severed nerve into one end of the tube and then the other end of the severed nerve into the other end of the tube, the nerve ends being in abutment within the tube. Additional means may be provided to maintain the nerve ends in abutment within the tube when required and means may also be provided facilitating removal of the tube upon repair of the nerve if desired.

1 Claim, 12 Drawing Figures

METHOD AND MEANS FOR THE REPAIR OF PERIPHERAL NERVES

The government has rights in this invention pursuant to Grant No. GH-33873 awarded by the National Science Foundation.

REFERENCE TO RELATED APPLICATION

This is a continuation-in-part application of the copending application in the name of the same inventor, filed Nov. 9, 1973, Ser. No. 414,246 and entitled METHOD AND MEANS FOR THE REPAIR OF PERIPHERAL NERVES, now U.S. Pat. No. 3,916,905 issued Nov. 4, 1975.

BACKGROUND OF THE INVENTION

1. Field of the Invention

The invention relates to the repair of accidentally severed nerves and more particularly to a method and means for accomplishing this end.

2. Description of the Prior Art

The method and means of the present invention may have a wide variety of applications including vascular repair and the like. While not intended to be so limited, for purposes of an exemplary showing the invention will be described in its application to the repair of severed mammalian peripheral nerves.

Many methods have been utilized to promote or facilitate nerve regeneration in peripheral nerve injuries. Unfortunately, despite advanced surgical techniques and use of the operating microscope, the results of peripheral nerve surgery in general have not improved greatly.

The problem of peripheral nerve regeneration has been studied intensively by many investigators and has been found to depend on many factors. The most important of these are the patient's age, type of injury, length of the nerge gap, nutrition of the nerve, amount of scar tissue, and finally, the technique of nerve repair. A repair is satisfactory when it is executed with as little trauma as possible and when anatomic approximation is achieved. It is difficult to fulfill the requirements without magnification, micro-surgical instruments, and the finest of sutures. Despite the advances that have been made to date, the re-establishment of normal function in the damaged nerve is considered poor. If results are to improve, in addition to gaining greater understanding of the physiology, the pathology of neural tissue and processes of nerve regeneration, it will be necessary to attain greater sophistication in the surgical manipulation of nerve tissue. It is to this latter goal that the present invention is directed.

While not so limited, the present invention is particularly advantageous in the repair of small nerves, that is, nerves 2 mm in diameter and less. Prime applications of the method of anastomosis of the present invention are the repair of digital and facial nerves. Digital nerves are the most frequently severed peripheral nerves, and though small in size are of critical importance because of their properties of discriminatory touch. Injury to facial nerves, though less common, is of serious consequence because of loss of communication through expression, interference with speech and activities as eating, drinking, and the like, as well as psychological effects.

The most critical factor of technique in neurorrhaphy is the accurate approximation of the cut ends of the fascicles (nerve bundles within the nerve trunk). Even though other factors may be ideal, the neurorrhaphy will fail if a significant number of fascicles do not match up. This is because motor axons regenerating through the sheaths of sensory nerves and vice versa will give no return of sensory or motor function. The fascicles of the larger nerves, such as the median and ulnar nerve, are large enough in cross sectional area that the cut ends of individual fascicles can be matched up by using the epineural vascular pattern for rotational orientation and microsurgical suture techniques. The fascicles of the small diameter nerves, however, are too small to be matched by suturing. The best that can be done is to match the nerve ends epineurium to epineurium using recognizable vascular patterns for rotational positioning. If the peripheral nerve is cleanly severed, a primary repair can be made with good approximation of the fascicles. However, if a segmental deficit exists, the likelihood of surgical orientation or matching of fascicles becomes increasingly less the greater the gap. This is attributed to the twisting and plexiform course of the fascicles and axons within the nerve trunk. It is apparent then, except in the instance of a clean cut followed by a primary repair, that a repair of a small nerve, successful in all other respects, will depend on the chances that the fascicles will match up, unless some natural mechanism exists for directing the axons to sheaths of their own kind. The problem of matching fascicles becomes less significant with the smaller nerves, since there are fewer fascicles, often no more than one, to contend with. Thus the chief hazard to the successful repair of fine nerves is the trauma produced by sutures and manipulation of the nerve and invasion of the field of regeneration by epineural and extraneural connective tissue. Many attempts have been made, almost entirely with larger nerves, to shield the region of anastomosis from connective tissue and facilitate longitudinal directional growth of the epineural and nervous tissue.

Of particular interest has been the use of other tissues or materials to form a channel through which the nerve fibers may grow and bridge the gap between the cut ends. Severed nerves have been drawn through blood vessels, or through decalcified bone tubes. Nerve fibers have also been wrapped in sheets of rubber, cargyl membrane, fascia lata or various other materials in an effort to reduce the ingrowth of scar tissue between the ends of the severed fibers. The methods employing organic materials have been relatively unsuccessful, largely because phagocytes have removed the nerve covering prematurely. More recently a tubulation method has found some success in neurorrhaphy whereby sheets of Silastic are wrapped about the anastomosis. This method facilitates regeneration of nerves, but suffers from the drawback of requiring the use of sutures. Methods employing adhesives, especially the cyanoacrylates, as a sutureless technique to anastomose severed nerves, though highly attractive have so far been ineffective.

The method and means of the present invention overcomes the above noted problems. The use of a porous bridge-conduit or tube prosthesis permits the cut ends of the nerve to be gently drawn into optimal proximity and secured in position without undue traumatic manipulation. Further, the prosthesis serves to reduce the effect of connective tissue (scar tissue), prevent neuromas, reduce edemal swelling and at the same time allow for escape of fluid exudates. The operational procedure is simple and can be quickly adapted by surgeons relatively inexperienced in performing neurorrhaphies.

The usefulness of such a prosthesis is obvious in any peripheral nerve injury or multiple injuries to the same nerve. It provides a stable bridge-conduit or tube for the regenerating proximal stump to grow through while retarding invasion of the tube by scar tissue.

SUMMARY OF THE INVENTION

The present invention contemplates the use of a bridge conduit in the form of a porous tube having an internal diameter of such size as to just nicely receive the proximal and distal ends of a severed peripheral nerve. An applicator instrument connected to a vacuum source is provided for manipulation of the tube.

When the tube is held in place on the instrument a transverse perforation in the tube wall enables a pressure differential to be developed between the interior of the tube and the ambient atmosphere through the agency of the vacuum source. The tube is so manipulated by the instrument that one end of the nerve is drawn into a first end of the tube. Thereafter, the other end of the nerve is caused to be drawn into the second end of the tube until the nerve ends are in a position of approximation within the tube. The vacuum source is then de-energized or disconnected and the tube is released by the instrument. The tube may be released by the instrument prior to de-energizing or disconnecting the vacuum source as will be developed hereinafter.

When desired, it is within the scope of the invention to utilize appropriate adhesives in conjunction with the tube to assure that the nerve ends remain in their position of approximation. Furthermore, the tube may be provided with means enabling its removal when repair of the nerve has been accomplished.

DESCRIPTION OF THE PREFERRED EMBODIMENTS

When a mammalian peripheral nerve is severed, the function supplied by that nerve, both motor and sensory, is lost. The nerve cells' appendages (axons) in the distal (the furthest away from the spinal cord) position of the severed nerve degenerate and die leaving only the sheaths in which they were contained. The axons in the proximal stump that are still connected to the spinal cord or dorsal root ganglion, also suffer some degeneration. The degeneration generally does not proceed to the death of the entire nerve cell bodies. However, if the injury occurs far enough from the nerve cell bodies, regeneration will occur. Axonal sprouts (branches or streams of axoplasma) will appear from the tip of the regenerating axon. These sprouts grow distally and attempt to reenter the intact neurilemmal sheaths of the distal portion of the severed nerve. If entry is successfully made, axonal growth will continue down these sheaths and function will eventually be restored.

Such injuries are commonly repaired by approximating the severed nerve stumps with sutures through the epineurium. However, the very act of suturing destroys nerve fibers. Only the larger nerves can be sutured without serious damage to axons, and even these require a highly skilled surgeon.

The present invention is directed to the development of a method and means for sutureless nerve repair utilizing a porous bridge conduit or tube-like element. A number of considerations enter into the development of such a system of nerve repair.

For example, there are two sources of proliferating tissue which can interfere with an misdirect axons migrating into the distal stump. Extraneural connective tissue may enter the field of regeneration and distort the pattern of regeneration. Such tissue may also constrict the axons and reduce function as a consequence of the damage done by the scar tissue during healing. Prior art workers have determined that most of the proliferating tissue interfering with the healing of a transected nerve is derived from the epineurium. Collagenization appears to spread out from the nerves into the surrounding tissue and the nerve itself is richly endowed with fibrocytes which rapidly re-establish the normal growth pattern of the stroma of the nerve. Much of the proliferating tissue which bridges the gap between the nerve ends is peripheral to the sutures in the epineurium. As this tissue increases in volume it tends to impress the suture material into the endoneurium, thereby decreasing the cross sectional area within the sheath available for regenerating axons. Hence, the less suture material present, the more this effect will be minimized.

The interconnecting porosity of the wall of the tube of the present invention must be sufficiently fine to prevent infiltration and plugging of the pores by extraneural and epineurial tissue. Infiltration of the pores, especially by epineural tissue would make it difficult to remove the tube if this is necessary. For example, a pore size of 20 to 30 $\mu$ has been found to be small enough to prevent ingrowth of bone tissue into the interstices of porous tube. On the other hand, if the porous tube can be left permanently in place, it may be that larger pores are desirable for promoting tissue ingrowth as a means of relieving pressure on the nerve. In summary, since the porous tube shields the nerve ends from extraneural connective tissue, avoids the occurrence of adhesions between the inner wall of the porous tube and epineural tissue, directs the growth of collagenous and nervous tissue, eliminates the use of suture material, and minimizes edemal swelling, the conditions for nerve regeneration are greatly enhanced.

It is known that a most important factor influencing the results of nerve repair is tension at the suture site. The amount of connective-tissue proliferation and the size of the gap between the stumps are directly related to the amount of tension present. For this reason it is important to provide for either no tension or slight compression in the segments of the nerve within the lummen of the porous tube.

It is necessary to bring the severed nerve ends together in a position as close as possible to their position before severance. This is especially important for larger nerves where it is desirable that the ends of severed fasciculi be matched as much as possible, especially with respect to motor and sensory bundles. For small diameter nerves where dissection of fasciculi and removal of epineurium is impractical, the use of a tube facilitates approximation of both fasciculi and their axons.

While not required, it is preferable that the tube be porous to provide for diffusion and flow of extracellular fluids that satisfy the nutritional requirements in the early stages of the regenerative process and before the blood supply is established. Porosity is also necessary to permit the free flow and escape of exudates from the site of nerve regeneration. In this way edemal swelling of the proximal axon endings may be minimized. Also, fluids that contribute to edemal swelling will not be trapped within the tube to cause damage to the nerves.

Nerve cells are very susceptible to changes in blood and oxygen supply, to bacterial toxins, viruses, chemicals, and toxic substances. For this reason, materials used in fabrication of the tube and in the system of securing the tubes to the nerve must not release toxic substances in the vicinity of the nerve. As already indicated, this problem has been avoided by employing a corrosion resistant alloy. The porosity aids in the removal of toxic substances by the fluids that permeate and flow through the porous tube walls.

Figure 1:
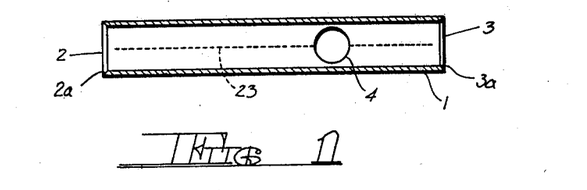
FIG. 1 is a longitudinal cross sectional view of the bridge conduit or tube of the present invention.

An exemplary tube for use in the present invention is illustrated in FIG. 1. The tube 1 is cylindrical, having open ends 2 and 3. While not required, the tube ends 2 and 3 may be flared as at 2a and 3a to facilitate entrance of the nerve ends therein.

The tube wall is provided with a transverse perforation 4. As will be described hereinafter, the perforation 4 enables the development of a vacuum or pressure differential within tube 1. The diameter of the perforation 4 will depend, in part at least, on the diameter of the nerve and hence the tube used. The perforation should be of such diameter as to permit the development of the above noted vacuum or pressure differential. However, the diameter should be sufficiently small to deter the pulling of the nerve end or portions thereof through the perforation 4.

The length and internal diameter of the tube 1 will be dictated primarily by the size of the nerve to be joined. The internal diameter of the tube should be such as to just nicely receive the severed nerve ends. The length should be such as to enable the tube to adequately hold the nerve ends in the desired position of approximation. Determination of proper length and internal diameter is well within the skill of the worker in the art.

Hereinafter, the method of the present invention and the use of the tube and applicator of the present invention will be described in terms of the repair of a sciatic nerve in the hind quarter leg of a Wistar strain laboratory rat. An adult rat of this type weighing approximately 200 gm. has a sciatic nerve of approximately 1 mm. in diameter. In such an instance, a tube having an internal diameter of from about 1 to about 1.2 mm. was found to serve the purpose well. Tubes having a length of from about 15 mm. to about 9.5 mm. proved adequate. It is preferable to use as short a tube as possible in an effort to minimize the amount of foreign material at the operated site.

The tube 1 may be made of any suitable material which will demonstrate the above mentioned characteristics and which will be compatible with the biological environment and be non-toxic. The tube must be free of residual substances which might react deleteriously with the nerve tissue or the biological processes contributing to healing. Good compatibility has been demonstrated by tubes made from fine powdered metal such as AISI Type 316 L stainless steel. Vitallium, a cobalt-chromium alloy manufactured by Austenal Laboratories, Inc., has also demonstrated good compatibility and a high degree of resistance to corrosion. Titanium or a titanium alloy such as Ti-6 Al-4 V is a preferred biomaterial for tube fabrication.

As indicated above, it is preferable to utilize tubes have a porous wall. The porosity of the tubes may range between 20 and 75%. In tubes used thus far in the practice of the present invention, the pores were elongated circumferentially and longitudinally as a consequence of the platelet shape of the particles from which the tubes were made and the nature of the tube forming process. Other pore and particle shapes and sizes may be used. In the tubes thus far used, the average length of the pores ranged from 8.4 to 14 $\mu$ and the width ranged from 2 to 2.5 $\mu$. The wall thicknesses of these tubes range from about 100 to about 125 $\mu$.

Figure 2:
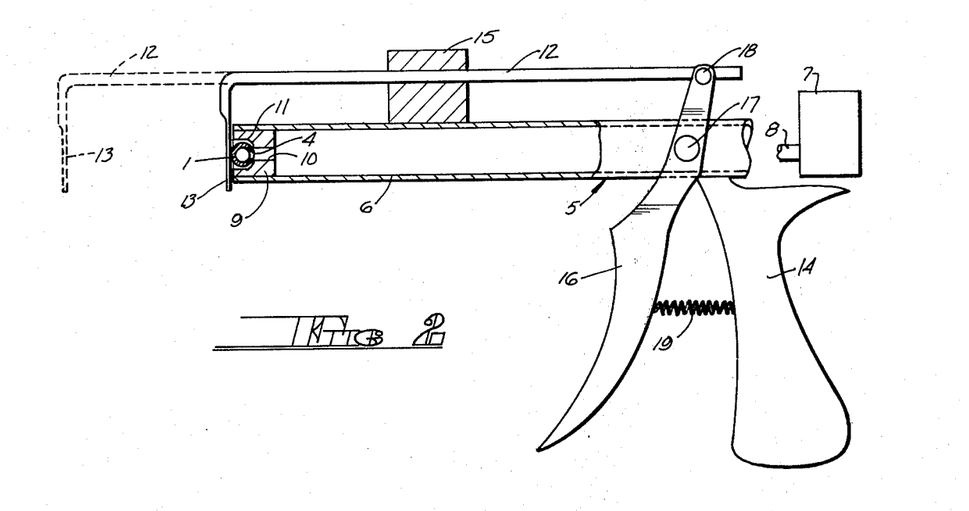
FIG. 2 is a fragmentary, semi-diagrammatic elevational view, partly in cross section, of the applicator instrument of the present invention illustrating the tube supported thereby.
Figure 3:
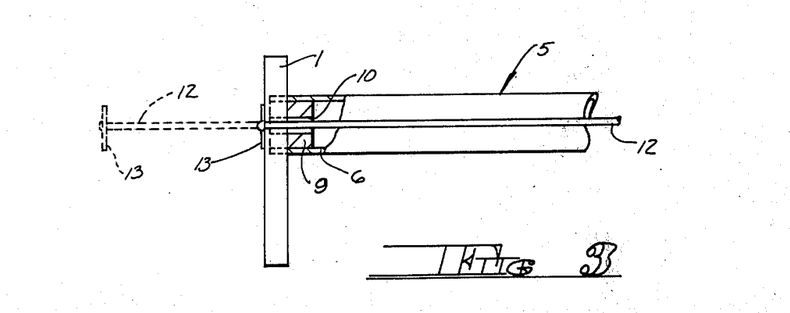
FIG. 3 is a fragmentary, semi-diagrammatic plan view, partly in cross section, of the forward end of the applicator instrument showing the tube supported thereby.

An applicator instrument for the tube of FIG. FIG. 1 is semi-diagrammatically illustrated in FIGS. 2 and 3. The instrument is generally indicated at 5 and comprises a hollow barrel 6. The barrel 6 is connected to a vacuum source diagrammatically indicated at 7 by means of a conduit 8. The forward end of the barrel is provided with a plug 9 having an axial hole 10 therethrough. The forward ends of the barrel and plug are notched transversely to form a seat 11 for the tube 1. When the tube 1 is to be supported by the instrument 5, it is placed in the transverse notch or seat 11 with its perforation 4 aligned with the axial hole 10 of the plug 9. This enables the above mentioned pressure differential to be developed in the interior of tube 1 through the action of vacuum source 7.

When the tube 1 is correctly placed in the seat 11, it is held in position by an appropriate releasable retaining means. In FIGS. 1 and 2, an exemplary retaining means 12 is illustrated in the form of a rod-like member extending longitudinally of and in parallel spaced relationship to the barrel 6. The rod-like retaining means 12 has a downwardly depending forward end, flattened as at 13 so as to afford good contact with the tube 1 and to reduce the unit contact pressure.

In FIGS. 2 and 3, the retaining means 12 is shown in solid lines in its fully retracted or retaining position. In both FIGURES, the retaining means is shown in broken lines in its fully extended or releasing position. It will be evident from both of the FIGURES that when the retaining means is in its fully retracted or retaining position, there is a small clearance between it and the forwardmost ends of the barrel 6 and the plug 9. This assumes firm contact with the tube 1. The clearance between the forwardmost ends of barrel 6 and plug 9 and the portion 13 of the retaining means, on the other hand, should be sufficiently small that if for any reason the retaining means portion 13 came into abutment with the forwardmost ends of barrel 6 and plug 9, the tube 1 would not be fractured, broken, or crushed.

The precise configuration of the instrument 5 and its retaining means 12 does not constitute a limitation on the present invention. For purposes of an exemplary illustration, the instrument is shown provided with a handle means 14. It will be understood that some form of actuating means must be provided to shift the retaining means 12 between its retaining and releasing positions. Furthermore, it is preferable that the retaining means 12 be biased to its retaining position. To this end, the retaining means is illustrated as passing through a support and guide block 15 appropriately affixed to the barrel 6. The block or guide 15 will assure proper positioning and alignment of the retaining means. An exemplary actuating means for the retainer is shown in the form of a trigger-like structure 16 pivotally affixed to the barrel 6 as at 17 and pivotally connected to the retainer 12 as at 18. An exemplary form of biasing means for the retainer 12 is shown as a coil spring 19 extending between handle 14 and trigger 16. It will be evident that the spring 19 will tend to urge the trigger 16 away from handle 14 which, in turn, will bias the retainer 12 to its retaining position. However, if the trigger 16 is shifted toward handle 14 against the action of the spring 19, the retainer 12 will assume its releasing position shown in broken lines.

As indicated above, the method of the present invention and the use of the tube of FIG. 1 and applicator instrument of FIGS. 2 and 3, will be described in terms of an example of the repair of the sciatic nerve in the hind quarter leg of an adult Wistar strain laboratory rat. The sciatic nerve is approximately 1 mm. in diameter. The various steps of the example are diagrammatically illustrated in FIGS. 4 through 8.

EXAMPLE

Figure 4:
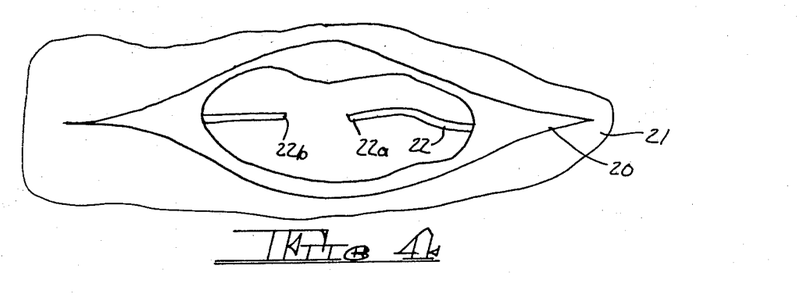
FIG. 4 is a diagrammatic plan view of a wound illustrating distal and proximal ends of an accidentally severed peripheral nerve.

Referring first to FIG. 4, an initial incision 20 is made in the skin 21 of the posterior thigh from the popliteal fossa to the base of the ischial tuberosity. The two heads of the biceps femoris are separated. The other hamstring muscles are not separated and are relatively undisturbed in the operation. The deep fascia is reflected with a curved hemostat to expose about 1 to 2 cm of the sciatic nerve 22. The nerve is carefully isolated by blunt dissection taking pains not to stretch it. Various methods have been used in an attempt to sever the nerve cleanly. The most effective to date has been to cut the nerve below the branch to short shsort head of the biceps femoris with a sharp surgical scissors. The severed ends 22a and 22b of the nerve retract leaving a gap of about 4–8 mm.

At this time the tube is fitted into the applicator instrument 5 which is connected to a pressure regulator (not shown), which in turn is connected to a vacuum source 7. It has been determined that a negative pressure of from about 5 to about 2.8 psi upstream of the instrument is sufficient to lift up the severed ends 22a and 22b of the nerve 22 and pull them down the tube 1 without causing any noticeable degree of trauma.

Figures 5, 6, 8:
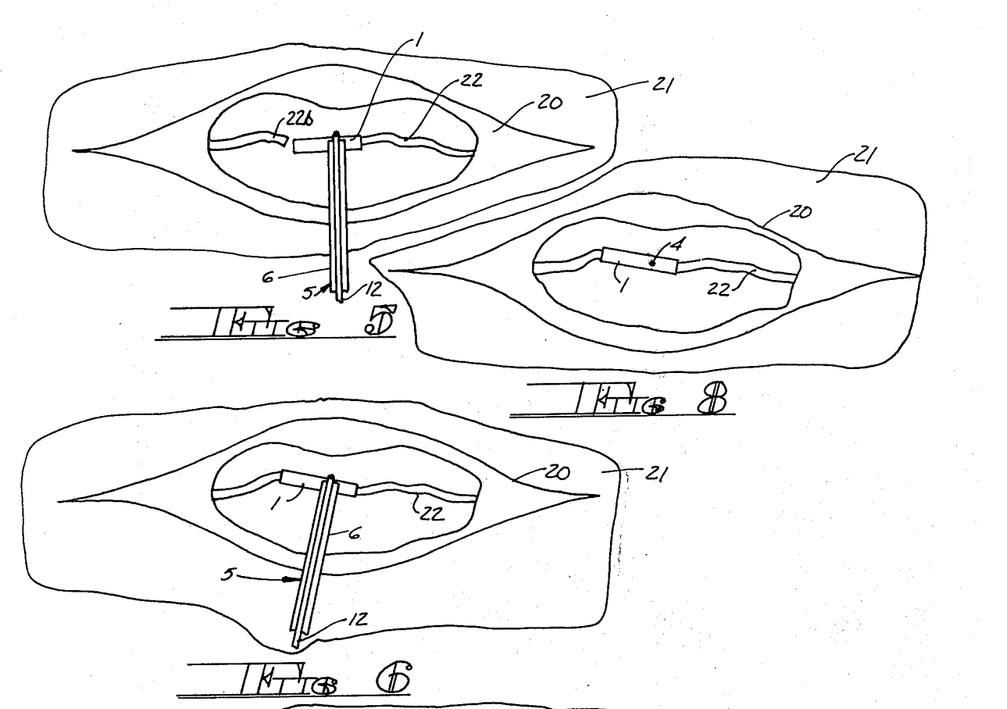
FIGS. 5 through 8 are diagrammatic plan views similar to that of FIG. 4 illustrating the repair of the nerve in accordance with the teachings of the present invention.
Figure 7:
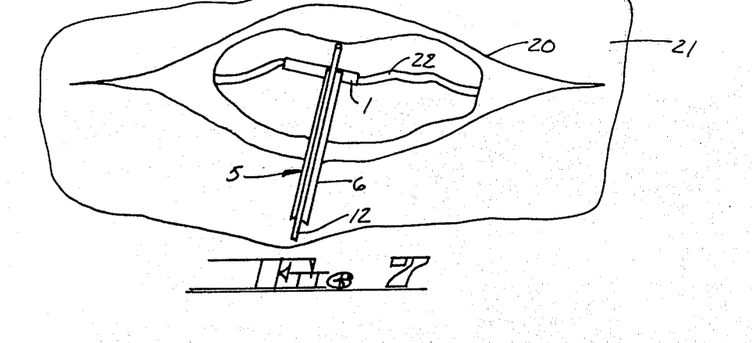

The forward end of the applicator instrument 5 is carefully placed in the open wound and one end (e.g. proximal end 22a) of the nerve pulled into the tube first without any manipulation of fingers or instruments (see FIG. 5). The distal end 22b is pulled into the tube in a similar manner (see FIG. 6). Under optimal conditions the operator is aware of the nerves being pulled into the tube both visually and by the very delicate vibratory sensations set up in the tube when the nerves meet or are in very close approximation.

The vacuum is thereafter turned off; the trigger mechanism of the applicator is activated (see FIG. 7), the tube is released from the applicator, and the applicator withdrawn from the operated site (see FIG. 8). The nerve ends will remain in situ inside the tube if the internal diameter of the tube is just tight enough to secure them and if no significant tension force is applied to the nerve.

Adhesives from the cyanoacrylate homologous series have been used to insure that the nerve ends will remain secure in the tube. Precautions should be taken to assure that no adhesive enters the tube and particularly that no adhesive reaches the nerve ends. Best results are obtained when the adhesive is applied sparingly with an appropriate applicator to the ends of the tube 1 and the adjacent portions of the nerve after the nerve ends are in place within the tube. Often good results are obtained without the adhesive, and in certain optimal circumstances it may not be necessary to use an adhesive.

Veterinary penicillin is placed in the wound, one I.U. by drop, and one I.U. is injected I.M. into the other extermity. The wound is then sutured with nylon suture and the animal is given the usual postoperative care.

In the foregoing example, the tube of the type and size described above was fabricated by powder metallurgy means. Such tubes have been found to demonstrate sufficient strength to rigidly support and shield the joined nerve ends against bending and crushing forces exerted externally as well as internally.

In FIG. 1 the perforation 4 is illustrated as being located approximately one-third the length of the tube 1 from the tube end 3. The placement of the perforation 4 in the tube is not a limitation on the present invention. Referring to FIGS. 1 and 5 through 7, it will be noted that if the perforation 4 is located as illustrated, a greater suction will be produced at the end 3 of the tube than at the end 2. If the first end to be introduced into tube 1 is introduced via end 3, its entrance will be somewhat facilitated. With the end 3 blocked by this nerve end, the second nerve end will be drawn into end 2 of the tube with the full force of the suction. However, the method has been successfully practiced with the perforation 4 located intermediate the tube ends.

The end 3 having the shorter distance between the perforation 4 and the end 3 is preferentially used to draw the shorter segment of the exposed severed nerve into the tube 1.

In the practice of the method of the present invention, as described in the example above, it has been found that approximation of the nerve ends can be accomplished quickly with a minimum of manual manipulation. Through the use of the tube and applicator instrument, anastomoses can be completed in less than 1 minute.

The above noted method has been practiced on a number of test rats and a high degree of functional integrity has been restored to a number of the animals before the sacrificing thereof after 100 to 120 days. In those animals where the recovery of function was less than desired, the failure could be attributed to several mechanical and toxicological causes including failure to bring the nerve ends into abutment, damage to nerve tissue caused by toxins from excessive amounts of adhesive, invasion and blockage of the field of regeneration by excessive amounts of adhesive and the like. Comparisons of dissected nerves of normal limbs and anastomized nerves after 120 days showed that there is only a slightly discernible indication of the cut line in the anastomized nerves. An experimental animal was not sacrificed and has lived for more than a year after being subjected to the method described in the example above, enjoying full use of its leg containing the repaired nerve.

Under some circumstances, it may be desirable to remove the tube after the healing has progressed sufficiently. To this end, the tube may be provided with a pair of diametrically opposed, longitudinal micro-slots extending nearly to the tube ends. One such micro-slot may be made in any suitable manner, as by a spark discharge machine technique well known in the art. The provision of the micro-slot enables the separation of the tube into two longitudinal halves by a careful tearing procedure without damage to the nerve.

Figures 9, 11, 12:
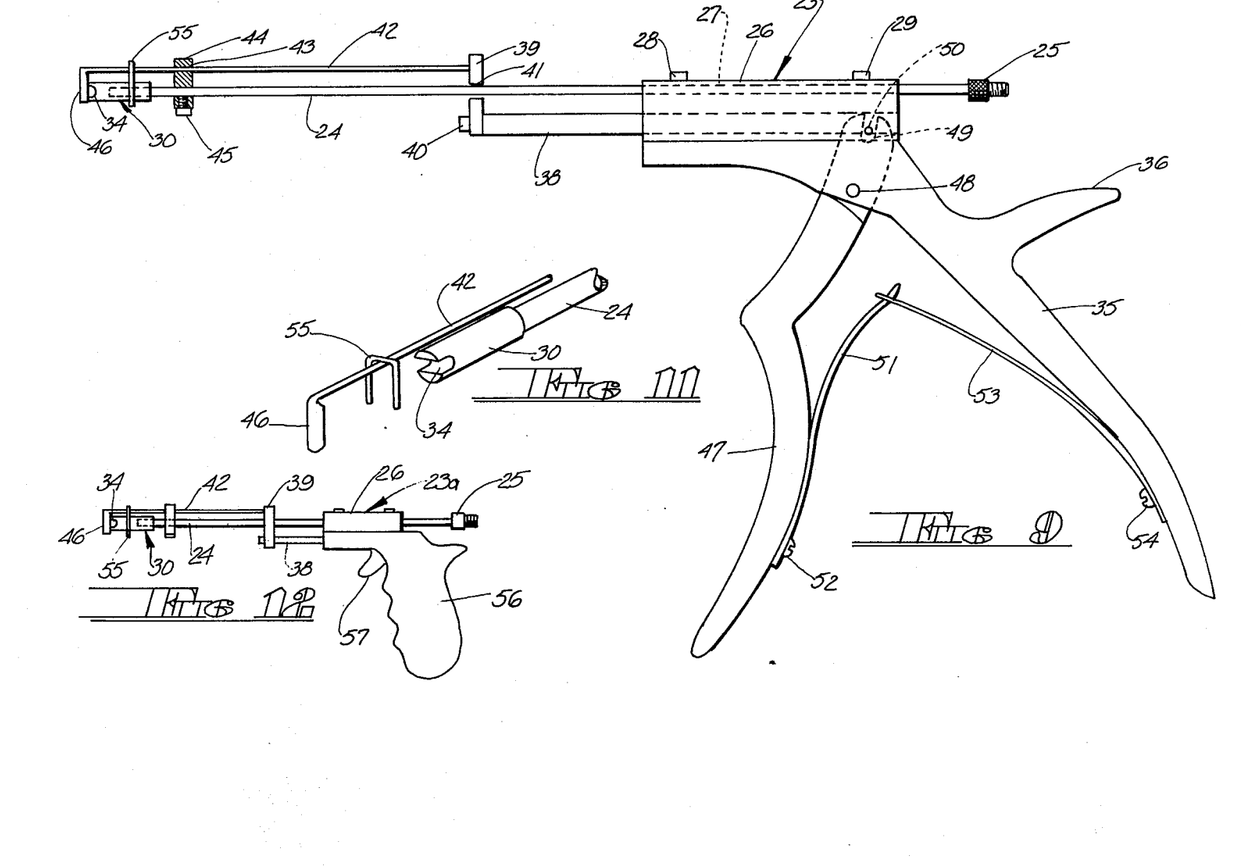
FIG. 9 is a side elevational view of another embodiment of the applicator instrument of the present invention.
FIG. 11 is a fragmentary perspective view of the forwardmost end of the instrument of FIG. 9 with the retaining means in its releasing position.
FIG. 12 is a side elevational view of an applicator instrument similar to that of FIG. 9 and provided with a pistol grip.
Figure 10:
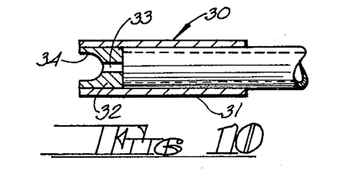
FIG. 10 is a fragmentary side elevational view, partly in cross section, of the forwardmost end of the instrument of FIG. 9 illustrating the adaptor therefor.

Modifications may be made in the invention without departing from the spirit of it. For example, FIGS. 9 through 11 illustrate an improved applicator instrument of the general type shown in and described with respect to FIGS. 2 and 3. The instrument is generally indicated at 23 and comprises a hollow barrel or tube 24 terminating at its rearward end in a fitting 25 by which the tube 24 can be connected to a flexible conduit leading to a vacuum source (see FIG. 2). The fitting 25 may be of any appropriate type and is conventional.

The instrument has a body portion 26 provided with a longitudinal perforation 27 through which the barrel 24 extends. While the barrel 24 may be permanently affixed within the perforation 27, for purposes of an exemplary showing it is illustrated as being maintained in place by set screws 28 and 29.

As is most clearly seen in FIG. 10, the forwardmost end of barrel 24 carries an adaptor generally indicated at 30. In the embodiment shown, the adaptor 30 comprises a tube 31 having a plug 32 at its forward end. The plug is provided with an axial hole 33 and the forwardmost ends of the tube 31 and plug 32 are notched as at 34. The notch 34 is equivalent to the notch 11 of FIG. 2 and serves as a seat for a tube or bridge conduit of the type shown in FIG. 1. As explained with respect to FIGS. 2 and 3, when a bridge conduit of the type shown in FIG. 1 is located in the notch or seat 34 of adaptor 30, its peripheral perforation or vacuum port 4 will be aligned with the axial hole 33 in plug 32 so that a pressure differential may be developed in the interior of the bridge conduit through the action of vacuum source 7.

The adaptor 30 is configured to be received on the forwardmost end of barrel 24, with the forwardmost end of barrel 24 in abutment with plug 32. Any suitable means may be used to maintain the adaptor in position on barrel 24. For example, the adaptor may have a frictional engagement with barrel 24 as illustrated in FIG. 10.

It will be understood that the instrument of FIG. 9 could have a seat for the bridge conduit or tube formed directly in its forwardmost end in the manner shown in FIG. 2. However, by the use of adaptors of the type shown in FIG. 10 having transverse notches or seats 34 of various predetermined sizes, the same instrument 23 may be used to apply bridge conduits or tubes of various diameters depending upon the size of the nerve to be repaired. While the adaptors may be fabricated in the manner illustrated in FIG. 10, it is within the scope of the present invention to mold or otherwise form them of a suitable plastic material such as Teflon or the like.

The body 26 of the instrument 23 is mounted on a handle means 35 which may be provided with a steadying extension 36, if desired. The body 26 has a second longitudinal perforation 37 beneath and parallel to the perforation 27 and adapted to slidingly receive a rod-like member 38. The rod-like member bears at its forwardmost end an upstanding guide 39. The guide 39 may be permanently affixed to the rod-like member 38 or may be removably attached as by a screw 40. The guide 39 has a perforation 41 through which the barrel 24 passes with a sliding fit so that guide 39 may be shifted along barrel 24, as will be described hereinafter. Affixed to the upper portion of shiftable guide 39 there is a retaining means 42 similar to retaining means 12 of FIG. 3. The retaining means 42 passes with a sliding fit through a perforation 43 in a fixed guide 44 mounted on barrel 24. While fixed guide 44 may be mounted on barrel 24 in any appropriate permanent or adjustable manner, for purposes of an exemplary showing it is illustrated as being maintained in place by a set screw 45. The forwardmost end 46 of retaining means 42 depends downwardly and is flattened (see also FIG. 11) and is equivalent to the forwardmost end 13 of retaining means 12 in FIGS. 2 and 3.

The rod-like member 38, guide 39 and retaining means 42 constitute a retaining means assembly. Any appropriate trigger means may be provided to shift this retaining means assembly longitudinally of barrel 24 and body 26. For purposes of an exemplary showing, an elongated trigger 47 is illustrated having an upper portion passing through an appropriate slot in handle means 35 and into the instrument body 26. Trigger 47 is pivoted to the handle means 35 as at 48. The uppermost end of the trigger is notched as at 49 and engages a transverse pin 50 in the rearward end of the rod-like member 38.

In FIG. 9 the retaining means assembly is illustrated in its normal or retracted position. It will be evident that if trigger 47 is shifted toward handle means 35 the inter-engagement of the trigger means and pin 50 will cause the retaining means assembly to shift forwardly along barrel 24 causing forwardmost end 46 of the retaining means 42 to move away from adaptor 30. Return of trigger 47 to the position illustrated in FIG. 9 will cause the retaining means assembly to return to its normal position as illustrated.

As indicated above with respect to the embodiment of FIGS. 2 and 3, it is preferable to provide means to bias trigger 47 and the retaining means assembly to their normal positions shown in FIG. 9. To this end, a first leaf spring 51 may be affixed to trigger 47 by any suitable fastener such as screw 52 and a second leaf spring 53 is similarly affixed to handle means 35 by screw 54. The upper end of leaf spring 53 is bifurcated and is adapted to receive the upper end of spring 51 between the bifurcations. Springs 51 and 53 bias trigger 47 and the retaining means assembly to their normal positions illustrated in FIG. 9.

The use of the instrument illustrated in FIG. 9 is substantially identical to that described with respect to the instrument of FIGS. 2 and 3. Retaining means 42 is shifted away from adaptor 30 by trigger 47 and a tube or bridge conduit is located in notch or seat 34 with its vacuum port aligned with axial perforation 33 in the adaptor. The trigger 47 is thereafter released and the bridge conduit is firmly held in place by seat 34 by retaining means 42. Once the nerve ends have been appropriately located in the bridge conduit or tube, as described above, the trigger means 47 will be shifted toward handle means 35 against the action of springs 51 and 53 to release the bridge conduit from adaptor 30.

It is possible during the repair of a nerve for the bridge conduit or tube to become stuck in the seat 34 of adaptor 30 by virtue of blood or other body fluids. It is desirable in such an instance to release the bridge conduit from seat 34 with a minimum of manipulation to prevent the nerve from retracting and slipping out of the tube and to avoid trauma to the nerve ends. For this reason, retaining means 42 may be provided with a separating means 55 in the form of an inverted U-shaped element welded or otherwise affixed to retaining means 42. It will be noted from FIG. 9 that when retaining means 42 is in its normal position, the downwardly depending legs of separator means 55 will straddle adaptor 30 and will be located behind seat 34. When retaining means 42 is shifted to its releasing position, separator means 55 will shift forwardly of seat 34 as shown in FIG. 11. As separator means 55 shifts forwardly, its downwardly depending legs will engage the bridge conduit and gently dislodge it from seat 34. Since the bridge conduit will be contacted by both legs of separator means 55, it will be dislodged without twisting. The separator means 55 should be spaced from the end 46 of retaining means 42 by an amount permitting the bridge conduit or tube to be easily located in seat 34 of adaptor 30.

The provision of separator means 55 further enables removal of the bridge conduit from seat 34 while a vacuum is still being drawn through barrel 24 and adaptor 30 thereby helping to assure that the nerve ends remain properly located within the bridge conduit during removal thereof from the instrument. It will be understood by one skilled in the art that a separator means 55 could be applied to the retaining means 12 of FIG. 2 to serve the same purpose.

In some instances it may be desirable to provide the instrument of the present invention with a piston grip so that the instrument may be more firmly and steadily held, movement of the operator's trigger finger only being required. Such an embodiment is illustrated in FIG. 12. Like parts have been given like index numbers. The instrument of FIG. 12 differs from that of FIG. 9 only in the provision of pistol grip 56 and trigger 57. The manner in which trigger 57 shifts rod-like member 38 does not constitute a limitation on the present invention and it will be understood that means (not shown) will be provided to bias trigger 57 to its unactuated position.

Finally, as indicated above, the technique of the present invention may be applied to the repair of small diameter veins and arteries. The bridge conduit or tube, being rigid but porous, will not interfere with the permeability of the vessel, while imparting enough strength to the vessel to act as a protective shield while natural repair takes place.

In the repair of a vessel, the vessel would be tied off at appropriate positions from the severed ends. To avoid internal wrinkling and artificial surfaces, fluids would be introduced into the vessel adjacent the tube. Again, adhesives could be used to maintain the vessel ends in the tube, when required. After an appropriate time lapse, the vessel would be untied.

The embodiments of the invention in which an exclusive property or privilege is claimed are described as follows:

1. An applicator instrument for applying a tube to the ends of a severed nerve to hold said ends in abutment to effect a sutureless repair of said nerve, said applicator instrument comprising a hollow barrel having a forward end and a rearward end, said rearward end being connectable to a vacuum source, a transverse notch at said forward end of said barrel to receive said tube and serve as a seat therefor, an opening in the region of said seat communicating with the interior of said hollow barrel and with which an evacuation hole in the wall of said tube may be aligned whereby a pressure differential between the interior of said tube and the ambient atmosphere may be developed by means of said vacuum source to draw said nerve ends into said tube, and a retaining means to releasably maintain said tube in said seat.

2. The structure claimed in claim 1, wherein said retaining means comprises a rod-like element extending longitudinally of said barrel and having an angularly related forward end overlying said forward end of said barrel, said retaining means being longitudinally shiftable between a retaining position wherein said forward end is adjacent said forward end of said barrel and in abutment with said tube when said tube is located in said seat, and a releasing position wherein said forward end of said retaining means is spaced from said forward end of said barrel by a distance greater than the diameter of said tube, and means to shift said retaining means between said retaining and releasing positions.

3. The structure claimed in claim 1 wherein said barrel is supported on a pistol grip handle means.

4. The structure claimed in claim 1 including a cylindrical adaptor releasably mounted on said forward end of said barrel and being coaxial therewith, said adaptor having a forward end extending forwardly of said forward end of said barrel, said forward end of said adaptor having said seat forming transverse notch and said opening communicating with said interior of said hollow barrel.

5. The structure claimed in claim 2, including means to bias said retaining means toward said retaining position.

6. The structure claimed in claim 2, including separator means on said rod-like element for contacting said tube and removing said tube from said seat when said rod-like element is shifted from said retaining position to said releasing position, said separator means being located behind said seat when said rod-like element is in said retaining position.

7. The structure claimed in claim 4, wherein said retaining means comprises a rod-like element extending longitudinally of said barrel and having an angularly related forward end overlying said forward end of said adaptor, said retaining means being longitudinally shiftable between a retaining position wherein said forward end is adjacent said forward end of said adaptor and in abutment with said tube when said tube is located in said seat, and a releasing position wherein said forward end of said retaining means is spaced from said forward end of said adaptor by a distance greater than the diameter of said tube, and means to shift said retaining means between said retaining and releasing positions.

8. The structure claimed in claim 6 wherein said separator means comprises an inverted U-shaped element having downwardly depending legs located to either side of said forward end of said barrel and behind said seat when said rod-like element is in said retaining position.

9. The structure claimed in claim 7, including means to bias said retaining means toward said retaining position.

10. The structure claimed in claim 7, including separator means on said rod-like element for contacting said tube and removing said tube from said seat when said rod-like element is shifted from said retaining position to said releasing position, said separator means being located behind said seat when said rod-like element is in said retaining position.

11. The structure claimed in claim 10 wherein said separator means comprises an inverted U-shaped element having downwardly depending legs located to either side of said adaptor and behind said seat when said rod-like element is in said retaining position.

* * * * *